United States Patent [19]

Hewawasam et al.

[11] Patent Number: 5,348,960
[45] Date of Patent: Sep. 20, 1994

[54] IMIDAZO[4,5-B]QUINOLINYL OXY ALKYL TETRAZOLYL PIPERIDINE DERIVATIVES

[75] Inventors: Piyasena Hewawasam, Middletown; Nicholas A. Meanwell, East Hampton, both of Conn.

[73] Assignee: Bristol-Myers Squibb Company, New York, N.Y.

[21] Appl. No.: 114,262

[22] Filed: Aug. 30, 1993

Related U.S. Application Data

[63] Continuation of Ser. No. 862,682, Apr. 3, 1992, abandoned.

[51] Int. Cl.$^5$ .................. C07D 471/04; A61K 31/445
[52] U.S. Cl. ........................................ 514/293; 564/82
[58] Field of Search ........................... 546/82; 514/293

[56] References Cited

U.S. PATENT DOCUMENTS

| | | | |
|---|---|---|---|
| 3,932,407 | 1/1976 | Beverung, Jr. et al. | 260/256.4 |
| 4,256,748 | 3/1981 | Chodnekar et al. | 424/251 |
| 4,490,371 | 12/1984 | Jones et al. | 424/248.54 |
| 4,668,686 | 5/1987 | Meanwell et al. | 514/293 |
| 4,701,459 | 10/1987 | Meanwell et al. | 514/293 |
| 4,775,674 | 10/1988 | Meanwell et al. | 514/293 |
| 4,943,573 | 7/1990 | Meanwell | 514/253 |

FOREIGN PATENT DOCUMENTS

| | | |
|---|---|---|
| 1289137 | 8/1990 | Canada . |
| 153152 | 8/1985 | European Pat. Off. . |

OTHER PUBLICATIONS

S. Seiler et al., "Imidazoquinoline Derivatives: Potent Inhibitors of Platelet cAMP Phosphodiesterase which Elevate cAMP Levels and Activate Protein Kinase in Platelets," *Throm. Res.*, 672: 31–42 (1991).
Kozak, et al, *Bull. Intern. Acad. Polanaise*, 1930A: 423–438 (Chem. Abs. 25, 5400)(1990).
J. S. FLeming, et al., New Drugs Annual: Cardiovascular Drugs, Raven Press, 277–204 (1983).
J. S. Fleming, et al., "Antithrombotic Activity of BMY 43351, a New Imiadzoquinoline with Enhanced Aqueous Solubility," *Throm. Res.*, 63, 145–155 (1991).
Ikeda, et al., "Comparison of the Inhibitory Effects of Cilostazol, Acetylsalicylic Acid and Ticlopidine on Platelet Functions ex vivo," *Arzeim.-Forsch./Drug Res.*, 37: 563–566 (1987).
Tanaka, et al., "Effects of a Selective Inhibitor of Cyclic AMP Phosphodiesterase on the Pial Microcirculation in Feline Cerebral Ischemia," *Stroke*, 20: 668–673 (1989).
Tanaka, et al., "Effects of Cilostazol, a Selective cAMP Phosphodiesterase Inhibitor on the Contraction of Vascular Smooth Muscle," *Pharmacology*, 36: 313–320 (1988).
Wantanabe, et al., *Arzneim.-Forsch./Drug. Res.*, 36: 1022–1024 (1986).
Shimizu, et al., "Physico–chemical Properties and Stability of Cilostazol," *Arzneim.-Forsch./Drug Res.*, 35 (II): 1117–1123 (1985).
Akiyama, et al., "The Absorption, Distribution and Excretion of a New Antithrombotic and Vasodilating Agent, Cilostazol, in Rat, Rabbit, Dog and Man," *Arzeim.-Forsch./Drug Res.*, 35 (II): 1124–1132 (1985).
Akiyama, et al., "The Metabolism of a New Antithrombotic and Vasodilating Agent, Cilostazol, in Rat, Dog and Man," *Arzeim.-Forsch/Drug Res.*, 35 (II): 1133–1140 (1985).
Usuda, et al., "The Localization of a New Antithrombotic Agent, Cilostazol, in CHO-K1 Cells as Demonstrated by Autoradiography," *Arzeim.-Forsch./Drug Res.*, 35 (II): 1141–1143 (1985).
Kimura, et al., "Effect of Cilostazol on Platelet Aggregation and Experimental Thrombosis," *Arzeim.-Forsch/Drug Res.*, 35 (II): 1144–1149 (1985).
Kawamura, et al., "Effect of Cilostazol, a New Antithrombotic Drug, on Cerebral Circulation," *Arzneim.-Forsch/Drug Res.*, 35 (II): 1149–1154 (1985).
Kawamura, et al., "Effect of Cilostazol, a New Antithrombotic Drug, on an Experimental Model of Peripheral Circulation Insufficiency," *Arzneim.-Forsch./Drug Res.*, 35 (II): 1154–1156 (1985).

(List continued on next page.)

*Primary Examiner*—Marianne M. Cintins
*Assistant Examiner*—Phyllis G. Spivack
*Attorney, Agent, or Firm*—Prabodh I. Almaula

[57] ABSTRACT

A series of 1,3-dihydro-2H-imidazo[4,5-b]quinolin-2-ones having enhanced water solubility bioavailability and metabolic stability is disclosed in the Formula I

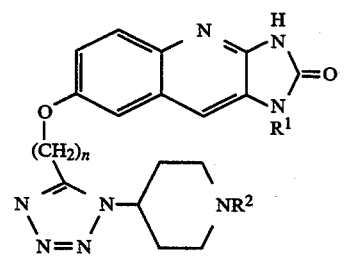

wherein
  $R^1$ is H, or $C_1$–$C_4$ lower alkyl;
  $R^2$ is H, or $(CH_2)_m R^3$;
  $R^3$ is tetrahydro-2H-pyranyl, $C_1$–$C_8$ alkyl, $C_4$–$C_8$ cycloalkyl, or substituted or unsubstituted phenyl, wherein the substituents are halogen, alkoxy, or trifluoromethyl;
  m is an integer of 1–3; and
  n is an integer of 1–5;
or pharmaceutically acceptable salt thereof.
  The compounds are useful as inhibitors of ADP-induced blood platelet aggregation in human platelet-rich plasma.

22 Claims, No Drawings

OTHER PUBLICATIONS

Shintani, et al., "General Pharmacological Properties of Cilostazol, a New Antithrombotic Drug, Part I," *Arzneim-Forsch/Drug Res.*, 35 (II): 1157–1162 (1985).

Shintani, et al., "General Pharmacological Properties of Cilostazol, a New Antithrombotic Drug, Part II," *Arzneim.-Forsch/Drug Res.*, 35 (II): 1163–1172 (1985).

Niki, et al., "Phase I Study of Cilostazol," *Arzneim.-Forsch./Drug Res.*, 35 (II): 1173–1185 (1985).

Yasunaga, et al., "Clinical Effects of Oral Cilostazol on Suppression of Platelet Function in Patients with Cerebrovascular Disease," *Arzneim-Forsch/Drug Res.*, 35 (II): 1186–1188 (1985).

Yasunaga, et al., "Antiaggregatory Effects of Oral Cilostazol and Recovery Platelet Aggregability in Patients with Cerebrovascular Disease," *Arzneim-.-Forsch/Drug Res.*, 35 (II): 1189–1192 (1985).

Kobayashi, et al., "Long-Term Effect of Cilostazol on Cerebral Blood Flow in Chronic Cerebral Infarction," *Arzneim.-Forsch./Drug Res.*, 35 (II): 1193–1197 (1985).

Yasuda, et al., "Hemodynamic Effect of Cilostazol on Increasing Peripheral Blood Flow in Arteriosclerosis obliterans," *Arzneim.-Forsch/Drug Res.*, 35 (II): 1198–1200 (1985).

Ohashi, et al., "Thermographic Evaluation of the Hemodynamic Effect of the Antithrombotic Drug Cilostazol in Peripheral Arterial Occlusion," *Arzneim.-Forsch/Drug Res.*, 35 (II): 1203–1208 (1985).

Kamiya, et al., "Hemodynamic Effects of the Antithrombotic Drug Cilostazol in Chronic Arterial Occlusion in the Extremities," *Arzneim.-Forsch./Drug Res.*, 35 (II): 1201–1203 (1985).

IMIDAZO[4,5-B]QUINOLINYL OXY ALKYL TETRAZOLYL PIPERIDINE DERIVATIVES

This application is a continuation, of application Ser. No. 07/862,682, filed Apr. 3, 1992, now abandoned.

BACKGROUND OF THE INVENTION

1. Field of the Invention

This invention relates to a new class of selective and potent inhibitors of platelet cyclic AMP phosphodiesterase is described. In particular, this invention relates to a series of new piperidinyl-, tetrazole derivatives of imidazo[4,5-b]quinolin-2-one which are useful as inhibitors of ADP-induced aggregation of human blood plateletes in platelet-rich-plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, intracranial tumors, thromboembolism, and hyperlipemia (A. Poplawski, et al, J. Atherosclerosis Research, 8: 721 (1968)).

The imidazo[4,5-b]quinolin-2-one derivatives have been identified as potent inhibitors of human blood platelet cAMP phosphodiesterase (PDE) and in vitro aggregation induced by adenosine diphosphate (ADP) and collagen (Seiler et al., Thromb. Res., 62, 31–42 (1991)).

The heterocycle "2,3-dihydro-2-oxo-1Himidazo[4,5-b]quinoline" of the formula (1), alternately referred to as 1,3-dihydro-2H-imidazo [4,5-b]quinolin-2-one, was described by Kozak, et al, Bull. Intern. Acad. Polanaise, 1930A, 432–438 (Chem. AbS. 25, 5400)

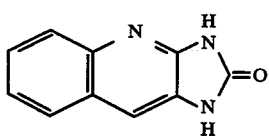

Derivatives of formula (1) having cyclic AMP phosphodiesterase inhibitory activity have been prepared and studied for their platelet inhibition and cardiotonic properties. Thus, for example:

Meanwell, N. A., U.S. Pat. No. 4,943,573 describes a series of 2,3-dihydro-2-oxo-1H-imidazo[4,5-b]quinolin-2-ones comprising derivative of the formula (2)

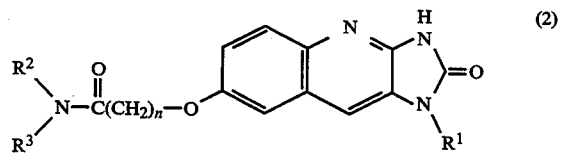

wherein n is 3 to 5; $R^1$ is hydrogen or alkyl of 1 to 4 carbon atoms; $R^2$ is hydrogen; $R^3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl; $R^2$ and $R^3$ together with the nitrogen atom to which they are attached form 4-$R^4$-piperazin-1-yl wherein $R^4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-$(CH_2)_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms.

Among the compounds disclosed is the compound of the formula (3), identified as 1-(cyclohexylmethyl)-4(2,3-dihydro-2-oxo-1H-imidazo[4,5-b]quinolin-7-yloxy)-1-oxybutyl]piperazine.

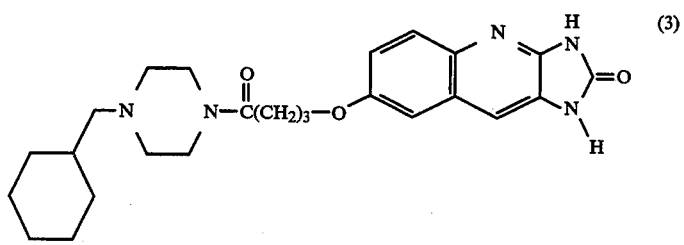

Meanwell, et al, U.S. Pat. No. 4,775,674 describe a series of 2,3-dihydro-2-oxo-1-H-imidazo [4,5-b]quinolinyl ether derivatives of the formula (4)

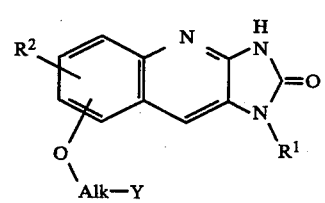

wherein $R^1$ is hydrogen, lower alkyl, benzyl; $R^2$ is hydrogen, halogen, lower alkyl, lower alkoxy; Alk is alkylene; Y is hydroxy and alkanoic or aralkanoic esters thereof, oxo ketone, dialkylamino carboxylic acid and esters, carboxamides, alkoxy, ethanolamines and cyclic carbamates thereof, tetrazoyl, and optionally substituted phenylsulfonyl.

Among the compounds disclosed is the compound of formula (5), identified in the art as 7-[4-(1-cyclohexyl-1H-tetrazol-5-yl) butoxyl] ]-1,3-dihydro-2Himidazo[4,5-b]quinolin-2-one.

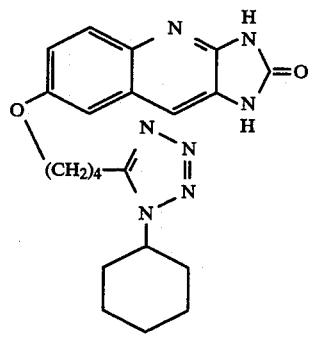

Meanwell, et al, U.S. Pat. No. 4,701,459 describe another series of 2,3-dihydro-2-oxo-1-H-imidazo-[4,5-b]quinoline compounds comprising amine derivatives of formula (6)

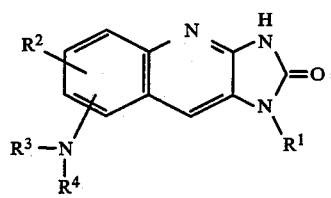

wherein $R^1$ is hydrogen, lower alkyl; $R^2$ is hydrogen, lower alkyl, lower alkoxy, halogen; $R^3$ is hydrogen, lower alkyl; $R^4$ is hydrogen, lower alkyl, alkanoyl, phenylalkanoyl wherein phenyl is optionally substituted with halogen, lower alkyl, lower alkoxy, $R^3$ and $R^4$ are joined together to form morpholinyl, piperidinyl or pyrrolidinyl optionally substituted with —$CO_2R^5$ or

wherein $R^5$ is hydrogen or lower alkyl, and $R^6$ is hydrogen, lower alkyl, cycloalkyl; 4-$R^7$-piperazinyl wherein $R^7$ is —$CO_2R^8$ wherein $R^8$ is lower alkyl phenyl optionally substituted with up to 2 halogen, lower alkyl or lower alkoxy: phenylalkanoyl of 7 to 10 carbon wherein phenyl is unsubstituted or independently substituted with up to 2 halogen, lower alkyl, lower alkoxy.

Meanwell, et al, U.S. Pat. No. 4,668,686 describe still another series of 1,3-dihydro-2H-imidazo-[4,5-b]quninolin-2-ones comprising derivatives of formula (7)

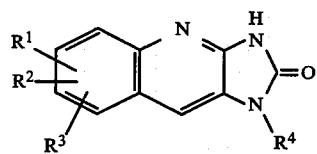

wherein $R^1$ is halogen, lower alkyl, lower alkoxy, trifluoromethyl; $R^2$ is hydrogen, halogen, lower alkyl, lower alkoxy; $R^3$ is hydrogen, halogen, lower alkyl, lower alkoxy; and $R^4$ is hydrogen or lower alkyl.

Another class of heterocyclic compounds having phosphodiesterase inhibiting and anti-platelet aggregation activity comprise the tetrahydroimidazo[2,1-b]quinazolin-2-ones of formula (8)

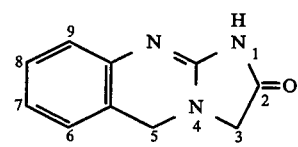

For example:

Beverung, Jr., et al, U.S. Pat. No. 3,932,407 disclose a series of compounds useful as blood platelet antiaggregative and/or antihypertensive and/or bronchodilator agents of tetrahydroimidazo[2,1-b]-quinazolin-2-one class. Anagrelide (9), a particularly preferred member of the Beverung, Jr., et al. series, has been studied extensively, e.g., J. S. Fleming, et al, New Drugs Annual: Cardiovascular Drugs, Raven Press, 277-294, N.Y. (1983).

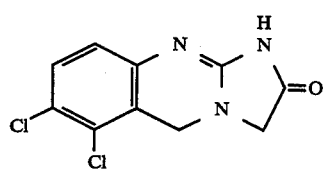

Chodnekar, et al, U.S. Pat. No. 4,256,748 describe a series of tetrahydroimidazo[2,1-b]quinazolin-2-ones of the formula (10) as inhibitors of the aggregation of blood platelets and cardiotonic activity.

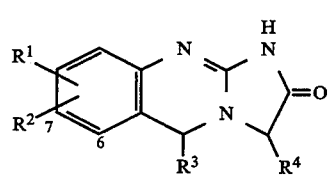

Representative of the Chodneker compounds are RO 15-2041 ($R^4$=$CH_3$, $R^3$=H, $R^2$=6—$CH_3$, $R^1$=7—Br) and RO 13—6438 ($R^4$=$CH_3$, $R^3$=H, $R^2$=6—$CH_3$, $R^1$=H)

Jones, et al, U.S. 4,490,371 describe another series of tetrahydroimidazo[2,1-b]quinazolin-2-one derivatives as cyclic AMP phosphodiesterase inhibitors useful as thrombogenic agents. Among the compounds disclosed is the formula (11) amide, identified in the art as lixazinone.

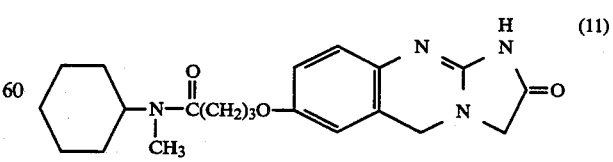

Jones, et al, European Patent Application 153152 further describe tetrahydroimidazo [2,1-b]quinazoline-ones of formula (11) as cyclic AMP phosphodiesterase inhibitors useful as antithrombogenic agents.

$$\underset{Y}{\overset{R^5-NCO(CH_2)_nO}{\text{(structure 12)}}}$$ (12)

Compounds of the aforementioned patents generally display limited solubility in water, acidic or alkali media and common organic solvents.

SUMMARY OF THE INVENTION

The present invention provides novel piperidinyltetrazole derivatives of imidazo [4,5-b]quinolin-2-one which are potent inhibitors of blood platelet aggregation and show good aqueous solubility.

In particular, the invention relates to a series of 7-oxypropyl-5-tetrazolyl-4-piperidinyl-1,3-dihydro-2H-imidazo[4,5-b]quinolin-2-ones wherein the cyclohexyl ring of the formula (5) compound was replaced with a piperidine moiety. The basic nitrogen atom of the piperidine ring provides a second site for salt formation resulting in enhanced potency and aqueous solubility compared to the formula (5) compound.

Formula I illustrates the compounds of the invention and the ring numbering system used herein.

Formula I

In the foregoing formula I, n, $R^1$, and $R^2$ are as described below.

The compounds of Formula I are useful as inhibitors of ADP-induced aggregation of human blood platelets in platelet rich plasma.

The compounds of Formula I have antithrombogenic and phosphodiesterase inhibition properties, and are useful in prevention or treatment of conditions involving platelet aggregation and thrombosis.

The compounds of Formula I are also considered to have antimetastatic potential in view of their platelet inhibition properties.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

DETAILED DESCRIPTION OF THE INVENTION

The compounds of the instant invention comprise those of Formula I

Formula I wherein
$R^1$ is H, or $C_1$–$C_4$ lower alkyl;
$R^2$ is H, or $(CH_2)_m R^3$;
$R^3$ is tetrahydro-2H-pyranyl, $C_1$–$C_8$ alkyl, $C_4$–$C_8$ cycloalkyl, or substituted or unsubstituted phenyl, wherein the substituents are halogen, alkoxy, or trifluoromethyl;
m is an integer of 1–3; and
n is an integer of 1–5;
or pharmaceutically acceptable salt thereof.

It is understood that as used herein limitation of Formula I are defined as follows:

The term "halogen" comprehends fluorine, iodine, bromine and chlorine, and most preferably fluorine and chlorine.

The term "$C_1$–$C_8$ alkyl" refers to a branched or unbranched saturated hydrocarbon chain containing from 1 to 8 carbon atoms, for example, methyl, ethyl, n-propyl, isopropyl, butyl, isobutyl, 3-pentyl, and 4-heptyl.

The term "$C_1$–$C_4$ lower alkyl" refers to a branched or unbranched saturated hydrocarbon chain containing from 1–4 carbon atoms, for example, methyl, ethyl, n-propyl, isopropyl, butyl and isobutyl.

The term "$C_4$–$C_8$ cycloalkyl" comprehends a saturated aliphatic ring containing the designated number of carbon atoms. Such radicals are, for example, cyclobutyl, cyclopentyl, cyclohexyl, cycloheptyl, and cyclooctyl.

According to the present invention, the compounds characterized by Formula I and the pharmaceutically acceptable acid addition salts thereof, were prepared as outlined in Scheme I.

Acylation of commercially available ethyl 4-aminopiperidinecarboxylate (2) with 4-chlorobutyryl chloride (1a) gave the corresponding amide 3a. The amide 3a was converted to corresponding iminoyl chloride with phosphorus pentachloride (PCl$_5$). In-situ prepared iminoyl chloride of the amide 3a was reacted with ozidotrimethylsilane (TMSN$_3$) to afford the tetrazole 4a. O-alkylation of 2-nitro-5-hydroxybenzaldehyde with the chloropropyl substituted terazole 4a provided the nitrobenzaldehyde derivative 5a. Condensation of anion of the phosphonate 6 with the aldehyde 5a afforded the isomeric mixture of hydantoin derivatives 7a,a'. Exhaustive catalytic hydrogenation over 10% palladium on activated carbon (Pd-C) followed by cyclization and concomitant oxidation using I$_2$ in methanol provided the target imidazoquinolin 10a. Basic hydrolysis of the carbamate moiety of 10a furnished the N-H congener 11a which was alkylated with variety of alkylating agents in the presence of triethylamine as the acid scavenger. Finally the target imidazoquinolines were converted to their dihydrochloride salts by reacting with anhydrous hydrogen chloride in methanol.

Scheme I
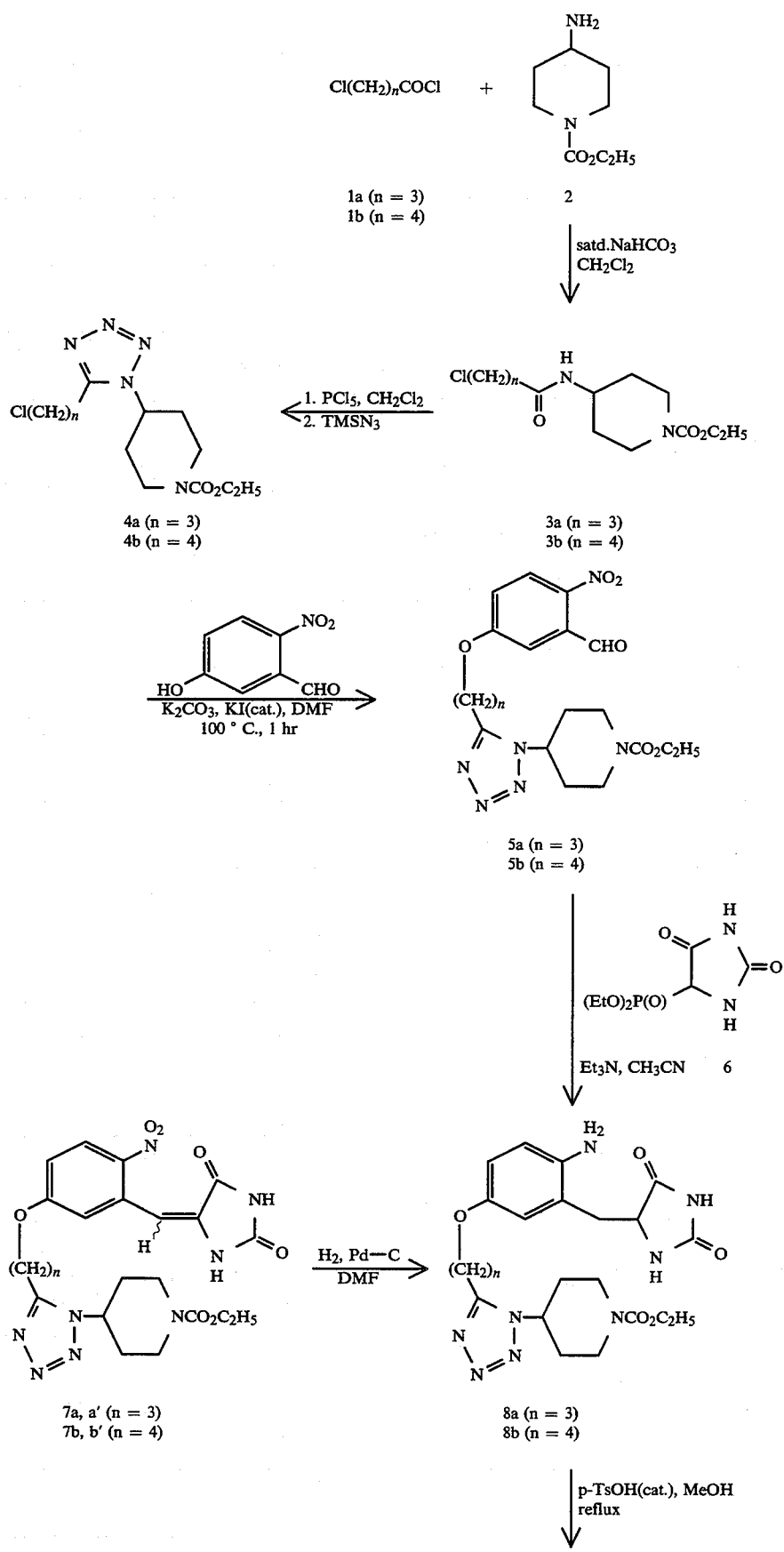

Scheme I

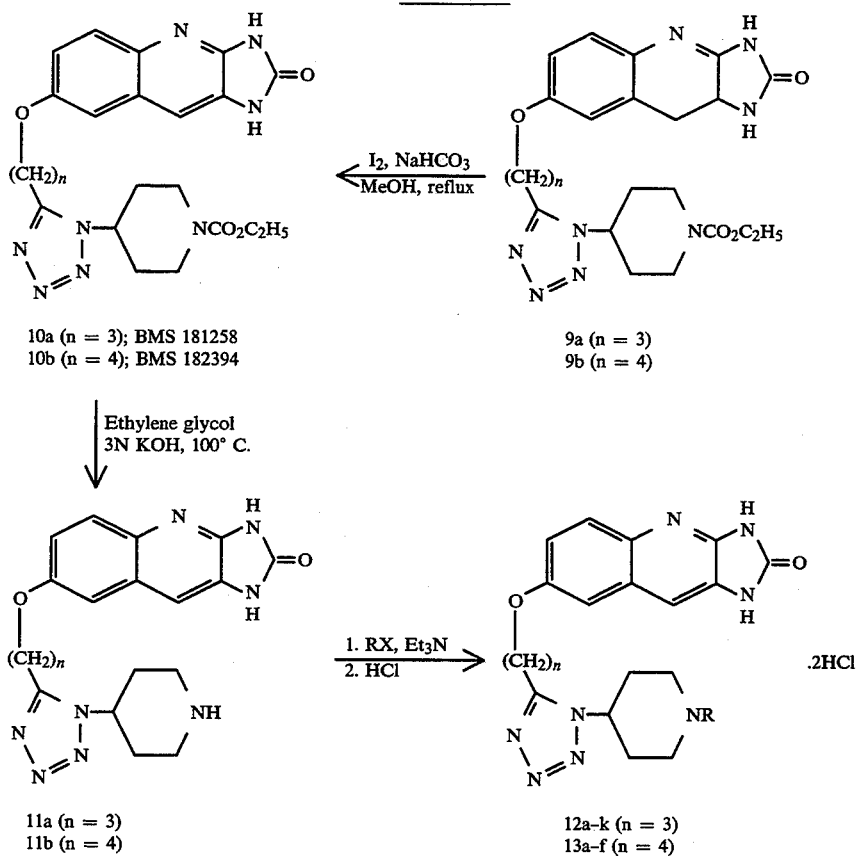

10a (n = 3); BMS 181258
10b (n = 4); BMS 182394

9a (n = 3)
9b (n = 4)

11a (n = 3)
11b (n = 4)

12a-k (n = 3)
13a-f (n = 4)

Vitro Inhibition of Human Platelet Aggregation

The aggregometer method of Born, C. V. R., J. Physiol., (London), 162, 67–68, (1962) as modified by Mustard, J. F., et al., J. Lab. Clin. Med., 64, 548–599, (1964) was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140xg) from citrated (3.8%) human blood. All glassware used for preparation of PRP is silicon treated. ADP in final concentration of 0.5 µg/mL or 0.05 mL of a collagen suspension prepared according to the method described by Evans, G., et al., J. Exp. Med., 128, 877–894, (1968) was used to induce aggregation. The various compounds tested were dissolved in dimethylsulfoxide (DMSO) so that 5 µl added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 µg/ml vs. ADP and 245 µg/ml vs collagen. Results for 50% inhibition of ADP-induced aggregation are given hereinafter.

The target compounds were evaluated as inhibitors of ADP-induced aggregation of human blood platelets in The target compounds were evaluated as inhibitors of ADP-induced aggregation of human blood platelets in platelet-rich-plasma (PRP) in vitro. The test compounds were incubated at about 37° C. in PRP for about 3 minutes prior to the addition of sufficient ADP to provide a final ADP concentration of 5.86 µM.

TABLE I

Inhibition of ADP-induced Human Platelet Aggregation by Test Compounds

| Cmpd # | $IC_{50}$ vs ADP in human PRP, µg/mL | Aqueous Solubility mg/mL |
| --- | --- | --- |
| 10a | 0.2 | 0* |
| 10b | 0.05 | 0* |
| 12a | 5.4 | >20 |
| 13a | 2.6 | ~5 |
| 12b | 0.022 | >10 |
| 13b | 0.018 | >5 |
| 12c | 0.019 | >10 |
| 13c | 0.031 | >5 |
| 12d | 0.009 | >10 |
| 13d | 0.012 | >5 |
| 12e | 0.007 | >10 |
| 13e | 0.0068 | >5 |
| 12f | 0.005 | >10 |
| 13f | 0.005 | >10 |
| 12g | 0.048 | <5 |
| 12h | 0.005 | 2–3 |
| 12i | 0.01 | ~1 |
| 12j | 0.048 | ~2 |
| 12k | 0.04 | >10 |

*Aqueous Solubility of Free Base

The Formula I compounds or pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the does of the compound which is thought to be effective and then increasing the dosage in small increments until the desired effect is achieved.

In carrying out the instant therapeutic methods, the active ingredient of Formula I and pharmaceutically acceptable acid addition slats thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

[(1-Ethoxycarbonyl) piperidin-4-y! ]-4-chlorobutyramide (3a)

A solution of ethyl 4-amino-1-piperidinecarboxylate (23.2 g, 0.135 mol) in ethylene chloride ($CH_2Cl_2$) (50 ml) was added rapidly to a stirred hi-phase mixture of 4-chlorobutyryl chloride (22.8 g, 0.162 mol) in $CH_2Cl_2$ (200 ml) and saturated sodium bicarbonate ($NaHCO_3$) solution (17 g in 200 ml of water). Resultant mixture was stirred at room temperature for about 3 hours. Layers were separated and the $CH_2Cl_2$ layer was washed consecutively with 1N $HC_1$ (100 ml), satd. $NaHCO_3$ (100 ml), water (200 ml), satd. brine (100 ml) and then dried magnesium sulfate ($MgSO_4$). Filtration followed by rotary evaporation of $CH_2Cl_2$ gave 40.6 g of white solid which was recrystallized from EtOAc/hexanes to give 35.6 g (95.5%) of pure 3a: mp 115°–116° C.; IR (KBr, $cm^{-1}$) 3279, 1700, 1644, 1548, 1437, 1229, 1143; $^1H$ NMR (300 MHz, $CDCl_3$) δ 1.21 (3H, t, J=7.2 Hz), 1.27 (2H, m), 1.86 (2H, m), 2.06 (2H, m), 2.30 (2H, t, J=6.9 Hz), 2.85 (2H, t, J=11.7 Hz), 3.55 (2H, t, J=6.1 Hz), 3.89 (1H, in), 4.03 (2H, m), 4.07 (2H, q, t=7.2 Hz), 5.85 (1H, d, J=7.7 Hz); $^{13}C$ NMR (75 MHz, $CDCl_3$) δ 14.85, 28.29, 32.15, 33.45, 42.92, 44.70, 46.75, 61.60, 155.62, 171.23; MS m/e 277 ($MH^+$).

Anal. calcd. for $C_{12}H_{21}ClN_2O_3$: C, 52.08; H, 7.65; N, 10.12. Found: C, 52.23; H, 7.91; N, 9.89.

EXAMPLE 2

Ethyl 4-[5-(3-chloropropyl)-1H-tetrazol-1-yl]-1-piperidinecarboxylate (4a)

To a stirred cold (−5° to 0° C.) solution of 3a (25.0 g, 0.09 mol) in anhydrous $CH_2Cl_2$ (300 ml), $PCl_5$ (20.8 g, 0.1 mol) was added in one portion under nitrogen. Resultant mixture was allowed to warm to room temperature and stirred for about 2 hours. Reaction mixture was cooled to −5° to 0° C. and neat $TMSN_3$ (20.8 g, 0.18 mol) was added over about 15 minutes. The mixture was allowed to warm to room temperature and then stirred overnight. Reaction mixture was carefully neutralized with satd. $NaHCO_3$ solution (300 ml). Layers were separated and the $CH_2Cl_2$ layer was washed with water, brine and then dried ($MgSO_4$). Filtration followed by rotary evaporation of $CH_2Cl_2$ gave 28.2 g of colorless oil which was used in the next step without further purification. A small sample was purified by flash chromatography (silica gel, 5% MeOH in CHCl₃) for analysis: IR (KBr, cm⁻¹) 1696, 1514, 1432, 1474, 1386, 1238; ¹H NMR (300 MHz, CDCl₃) δ 1.22 (3H, t, J=7.1 Hz), 1.96 (2H, m), 2.13 (2H, m), 2.31 (2H, m), 2.95 (2H, m), 2.97 (2H, t, J=7.1 Hz), 3.62 (2H, t, J:5.8 Hz), 4.10 (2H, q, J=7.1 Hz), 4.28 (2H, m), 4.35 (1H, m); ¹³C NMR (75 MHz, CDCl₃) δ 14.56, 20.17, 29.20, 31.63, 42.49, 43.61, 55.34, 61.63, 152.88, 155.16; MS m/e 302 (MH+).

EXAMPLE 3

2-Nitro-5-[3-[1-[(1-ethoxycarbonyl)piperidin-4-yl]1H-tetrazol-5-yl-9 prop-3-yloxy]benzaldehyde (5a)

A stirred suspension of 5-hydroxy-2-nitrobenzaldehyde (14.95 g, 0,089 mol), the tetrazole derivative 4a (27.0 g, 0.089 mol), anhydrous potassium carbonate (K₂CO₃) (14.8 g, 0.107 tool) and KI (2.95 g, 0.018 tool) in anhydrous DMF (110 ml) was heated at about 100°–110° C. under nitrogen for about 1.25 hours. Reaction mixture was allowed to cool to about 50°–60° C. and then most of the DMF was removed by rotary evaporation (2–3 mmHg/50° C. bath temperature). Resultant viscous residue was suspended in CH₂Cl₂ (300 ml) and then water (~100 ml) was added and stirred thoroughly. Layers were separated and the aqueous layer was re-extracted with CH₂Cl₂ (2×200 ml). Combined CH₂Cl₂ extracts were washed consecutively with 10% sodium carbonate (Na₂CO₃) (3×200 ml), water, brine and then dried (MgSO₄). Filtration followed by rotary evaporation of CH₂Cl₂ gave viscous brown syrup which was kept in vacuo for about 2.5 days to provide a solid mass. Solid material was dissolved in CH₂Cl₂ and then reprecipitated by addition of hexanes to give 34.1 (91%) of fairly clean product which was used in the next step without further purification. mp 99°–101° C.; IR (KBr, cm¹) 1700, 1594, 1520, 1332, 1284, 1238, 852; 1H NMR (300 MHz, DMSO-d₆) δ 1.20 (3H, t, J=7.0 Hz), 1.86 (2H, m), 2.01 (2H, m), 2.27 (2H, m), 3.04 (2H, m), 3.13 (2H, t, J=7.4 Hz), 4.06 (2H, q, J=7.0 Hz), −4.1 (2H, m), 4.29 (2H, t, J=6.1 Hz), 4.72 (1H, m), 7.25 (1H, d, J=2.8 Hz), 7.35 (1H, dd, J=9.0 and 2.8 Hz), 8.19 (1H, d, J=9.0 Hz) 10.29 (1H, S); ¹³C NMR (75 MHz, DMSO-d₆) δ 16.29, 20.73, 27.45, 33.13, 43.94, 55.68, 62.63, 69.60, 115.82, 120.18, 129.07, 135.99, 143.61, 155.77, 156.29, 164.40, 191.65; 433 (MH+).

Anal. calcd. for C₁₉H₂₄N₆O₆: C, 52.77; H, 5.59; N, 19.43. Found: C, 52.45; H, 5.60; N, 19.46.

EXAMPLE 4

Ethyl 4-[5-[3-(2,3-dihydro-2-oxo-1H-imidazo[4,5-b]quinolin-7-yloxy) propyl ]-1H-tetrazol-1-yl ]-1-piperidinecarboxylate (1.0a)

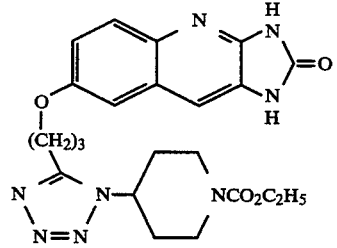

A solution of the aldehyde 5a (30.0 g, 0.069 mol) in acetonitrile (200 mL) was added dropwise over about 30 minutes, to a partial solution of the phosphonate 6 (19.6 g, 0.083 mol) and isoamylamine (Et₃N) (15.5 mL, 0.11 mol) in acetonitrile (100 mL). The resultant deep-red solution was stirred at room temperature under nitrogen for about 4.5 hours. Excess Et₃N and acetonitrile were rotary evaporated under reduced pressure (50° C. bath temperature). Resultant viscous brown-red oil was treated with 0.05N HCl (200 mL) with mechanical stirring. Initially formed gummy, lumps gradually breaks up into finely divided solid upon good agitation. Solid material was filtered, washed with water and then air dried overnight. Crude product was recrystallized from CH₂Cl₂/MeOH/hexanes to give about 34.1 g (96%) of pure 7a,a' which consist of mixture of olefinic isomers: IR (KBr, cm¹) 3600–2600, 1740, 1708, 1674, 1604, 1588, 1506, 1386, 1326, 1266, 1238, 838; MS m/e 515 (MH+).

Hydrogenation of 7a,a' (2×14 g) was carried in two equal batches. A suspension resulted from addition of about 10% Pd-C (0.7 g) to a solution of 7a,a' (14g) in dimethylformaldehyde (DMF) (200 mL) was hydrogenated in a Parr apparatus under 60–70 psi hydrogen pressure for about 7 hours. Then additional fresh Pd-C (0.7 g) was added and continued for additional 24 hours. TLC and NMR shows unreduced of olefin moiety. Fresh Pd-C (0.7 g) was added and continued for additional 17 hours. The suspension was filtered through a pad of celite and the celite filtercake was washed thoroughly with DMF. Combined filtrate and washings were rotary evaporated (2–3 mmHg, 50° C. bath temperature) to give a viscous oil which was kept in vacuo overnight to afford about 18–19 g of crude product from each batch. Combined crude product 8a was used in the next step without further purification.

The crude aniline derivative 8a (~37 g) was suspended in anhydrous methanol (800 mL) and p-TsOH (2.8 g) was added. Resultant suspension was magnetically stirred and heated to reflux for about 5 hours. Then solid NaHCO₃ (2 g) was added in small portions. Once the gas evolution is ceased, I₂ was added in small potions. Resultant brown mixture was heated to relfux overnight (15 hrs). Thin layer chromatography (TLC) shows absence of starting material. The methanol was rotary evaporated and the residue was neutralized with saturated NaHCO₃ solution (50 mL) and then treated with 10% sodium thiosulfate (Na₂S₂O₃) solution (200 mL). Resultant brown-gray suspension was stirred for about 0.5 hour. Precipitate was filtered, washed with water and then air dried overnight-Crude product was triturated with boiling methanol to afford about 21.3 g (84% overall for 3 steps) of pure 10a mp : 279°–281° C.; IR (KBr, cm¹) 3600–2600, 1728, 1692, 1454, 1242, 824; ¹H NMR (300 MHz, DMSO-d₆) δ 1.17 , (3H, t, J=7.1 Hz), 1,83 (2H, m), 1.97 (2H, m), 2.25 (2H, m), 2.95 (2H, m), 3.13 (2H, t, J=7.4 Hz), 4.03 (4H, m), 4.13 (2H, t, J=5.9 Hz), 4.69 (1H, m), 7.12 (1H, dd, J=9.1 and 2.7 Hz), 7.31 (1H, d, J=2.7 Hz), 7.49 (1H, s), 7.67 (1H, d, J=9.1 Hz), 10.94 (1H, s), 11.35 (1H, s); ¹³C NMR (75 MHz, DMSO-d₆) δ 14.58, 19.21, 26.21, 31.43, 42.21, 54.00, 60.91, 66.42 , 107.28, 109.44, 117.98, 125.10, 126.47, 128.17, 138.14, 145.45, 154.23, 154.53, 154.57, 155.42; MS m/e 467 (MH+).

Anal. calcd. for C₂₂H₂₆N₈O₄.0.28H₂O: C, 56.04; H, 5.68; N, 23.76. Found: C, 56.05; H, 5.49; N, 23.63.

EXAMPLE 5

[5-[3-(2, 3-Dihydro-2-oxo-1H-imidazo[4,5-b]quinolin-7-yloxy)-propyl]-1H-tetrazol-1-yl]piperidine dihydrochloride (12a)

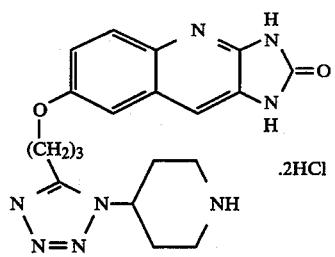

A stirred solution of 5 (19 g, 0.041 mol) in ethylene glycol (100 mL) and 3N KOH (50 mL) was heated at about 120° C. for about 15 hours under nitrogen. Reaction mixture was allowed to cool to room temperature and then acidified with 3N HCl to pH 2. pH of the resultant suspension was adjusted to 7–8 with saturated NaHCO3 solution. The precipitate was filtered, washed with water and then air dried overnight. Crude product was triturated with boiling methanol to give 15.3 g (95%) of free base of 6. A small sample (0.5 g) was converted to dihydrochloride salt by reacting with anhydrous HCl/MeOH.

mp 355°–357° C.; IR (KBr, cm$^{-1}$) 3600–2200, 1764, 1686, 1228, 832; $^1$NMR (300 MHz, DMSO-d$_6$) δ 2.15, (2H, m), 2.25 (4H, m), 3.05 (2H, m), 3.13 (2H, t, J=7.4 Hz), 3.36 (2H, m), 4.15 (2H, t, J=5.9 Hz), 4.90 (1H, m), 7.17 (1H, dd, J=9.1 and 2.7 Hz), 7.39 (1H, d, J=2.7 Hz), 7.64 (1H, s), 7.77 (1H, d, J=9.1 Hz), 9.2 (1H, brd s), 9.32 (1H, brd s), 9.53 (1H, brd s), 11.33 (1H, s); $^{13}$C NMR (75 MHz, DMSO-d$_6$) δ 19.29, 26.10, 28.28, 41.94, 51.58, 66.65, 107.60, 111.18, 118.69, 125.70, 126.06, 126.17, 135.05, 144.56, 154.46, 154.96, 154.99; MS m/e 395 (MH+).

Anal. calcd. for C$_{19}$H$_{22}$N$_8$O$_2$.2HCl: C, 48.83; H, 5.17; N, 23.97. Found: C, 49.08; H, 5.04; N, 23.89.

EXAMPLE 6

[5-[3-(2,3-Dihydro-2-oxo-1H-imidazo [4,5-b]quinolin-7-yloxy) propyl]-1H-tetrazol-1-yl]-1-(phenylmethyl) piperidine dihydrochloride (12b)

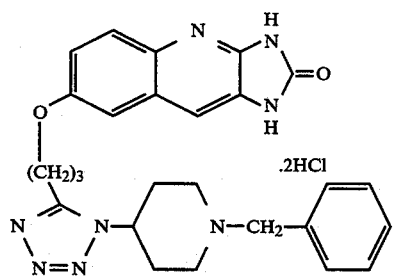

mp 273°–275° C.; IR (KBr, cm$^{-1}$) 3600–2400, 1720, 1624, 1242, 824, 750, 702; $^1$H NMR (300 MHz, DMSO-d$_6$) δ 2.22, (4H, m), 2.45 (2H, m), 3.09 (4H, m), 3.47 (2H, m), 4.13 (2H, t, J=5.9 Hz), 4.30 (2H, m), 4.80 (1H, m), 7.11 (1H, dd, J=9.1 and 2.7 Hz), 7.32 (1H, d, J=2.7 Hz), 7.45 (3H, m), 7.52 (1H, s), 7.60 (2H, m), 7.69 (1H, d, J=9.1 Hz), 11.06 (1H, s), 11.08 (1H, brd s), 11.4 (1H, brd s); $^{13}$C NMR (75 MHz, DMSO-d$_6$) δ 19.27, 26.11, 28.55, 49.83, 51.65, 58.69, 66.50, 107.34, 109.83, 118.11, 125.25, 126.40, 127.73, 128.81, 129.35, 129.60, 131.39, 131.68, 137.47, 145.28, 154.60, 155.34; MS m/e 485 (MH+).

Anal. calcd. for C$_{26}$H$_{28}$N$_8$O$_2$.2HCl.0.5 H$_2$O: C, 55.14; H, 5.52; N, 19.78. Found: C, 55.14; H, 5.79; N, 19.59.

EXAMPLE 7

[5-[3-(2, 3-Dihydro-2-oxo-1H-imidazo[4, 5-b]quinolin-7-yloxy) propyl]-1H-tetrazol-1-yl]-1-[(4-fluorophyl) methyl]piperidine dihydrochloride (12c)

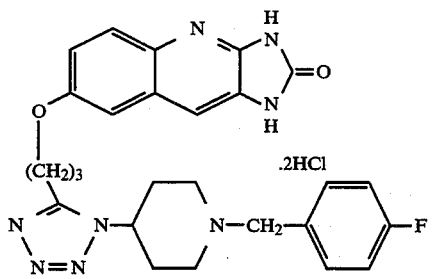

mp 255°–258° C.; IR (KBr, cm$^{-1}$) 3600–2300, 1746, 1642, 1228, 838; $^1$H NMR (300 MHz, DMSO-d$_6$) δ 2.18, (2H, m), 2.25 (2H, m), 2.48 (2H, m), 3.04 (2H, m), 3.11 (2H, t, J=7.3 Hz), 3.45 (2H, m), 4.13 (2H, t, J=6.0 Hz), 4.30 (2H, m), 4.77 (1H, m), 7.0 (2H, brd s), 7.13 (1H, dd, J=9.1 and 2.7 Hz), 7.30 (2H, t, J=8.8 Hz), 7.35 (1H, d, J=2.7 Hz), 7.57 (1H, s), 7.71 (3H, m), 11.14 (1H, s), 11.41 (1H, brd s); 13C NMR (75 MHz, DMSO-d$_6$) δ 19.29, 26.10, 28.53, 49.66, 51.70, 57.66, 66.57, 107.46, 110.31, 115.57, 115.86, 118.33, 125.43, 125.71, 126.36, 127.19, 134.06, 134.17, 145.08, 154.57, 154.76, 155.25; MS m/e 503 (MH+).

Anal. calcd. for C$_{26}$H$_{27}$FN$_8$O$_2$.2HCl.1.3 H$_2$O: C, 52.05; H, 5.33; N, 18.67. Found: C, 52.05; H, 5.34; N, 18.25.

EXAMPLE 8

(Cyclohexylmethyl)-4-[5-[3-(2,3-dihydro-2-oxo-1H-imidazo[4,5-b]quinolin-7-yloxy)propyl]-1H-tetrazol-1-yl]piperidine dihydrochloride (12d)

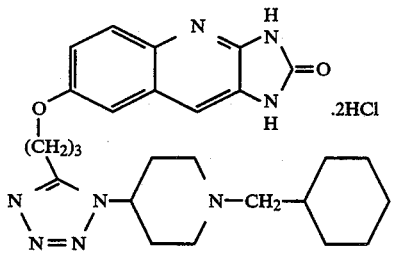

245°–250° C.; IR (KBr, cm$^{-1}$) 3600–2400, 1726, 1624, 1240, 822; $^1$H NMR (300 MHz, DMSO-d$_6$) δ 0.94, (2H, m), 1.15 (3H, m), 1.64 (3H, m), 1.85 (3H, ia), 2.15 (2H, m), 2.27 (2H, m), 2.61 (2H, m), 2.87 (2H, t, J=5.4 Hz), 3.07 (2H, m), 3.14 (2H, m), 3.58 (2H, m), 4.17 (2H, t, J=5.7 Hz), 4.84 (1H, m), 6.0 (1H, very brd s), 7.15 (1H, dd, J=9.1 and 2.7 Hz), 7.38 (1H, d, J=2.7 Hz), 7.59 (1 H, s), 7.73 (1H, d, J=9.1 Hz), 10.51 (1H, brd s), 11.21 (1H, s), 11.6 (1H, brd s); $^{13}$C NMR (75 MHz, DMSO-d$_6$) δ 19.38, 25.09, 25.53, 26.15, 28.45, 30.84, 32.30, 51.15, 51.90, 62.15, 66.62, 107.53, 110.32, 118.35, 125.47,

EXAMPLE 9

[5-[3-(2,3-Dihydro-2-oxo-1H-imidazo[4,5-b]quinolin-7-yloxy)propyl]-1 1H-tetrazol-1-yl]-1-(2-ethylbut-1-yl) piperidine dihydrochloride (12e)

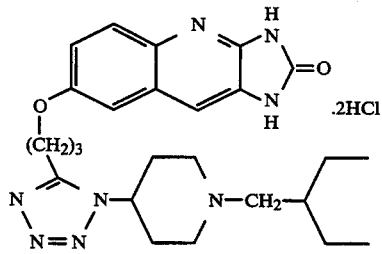

mp 253°–256° C.; IR (KBr, cm$^{-1}$) 3600–2400, 1742, 1624, 1364, 1236, 828; $^1$H NMR (300 MHz, DMSO-d$_6$) δ 0.83, (6H, t, J=7.3 Hz), 1.37 (4H, m), 1.73 (1H, m), 2.16 (2H, m), 2.27 (2H, m), 2.62 (2H, m), 2.91 (2H, t, J=5.7 Hz), 3.08 (2H, m), 3.15 (2H, m), 3.60 (2H, m), 4.16 (2H, t, J=5.8 Hz), 4.82 (1H, m), 7.0–7.5, (2H, brd s), 7.16 (1H, dd, J=9.1 and 2.7 Hz), 7.38 (1H, d, J=2.7 Hz), 7.61 (1H, s), 7.75 (1H, d, J=9.1 Hz), 10.47 (1H, brd s), 11.26 (1H, s); $^{13}$C NMR (75 MHz, DMSO-d$_6$) δ 10.15, 19.36, 23.26, 26.12, 28.41, 34.89, 51.15, 51.94, 59.82, 66.63, 107.55, 110.60, 118.46, 125.55, 126.32, 126.86, 136.20, 144.93, 154.58, 154.84, 155.18; MS m/e 479 (MH+).

Anal. calcd. for C$_{25}$H$_{34}$N$_8$O$_2$.2HCl.1.0 H$_2$O: C, 52.59; H, 6.73; N, 19.62. Found: C, 52.59; H, 6.70; N, 19.26.

EXAMPLE 10

[5-[3-(2,3-Dihydro-2-oxo-1H-imidazo[4,5-b]quinolin-7-yloxy)propyl]-1H-tetrazol-1-yl]-1-(2-methylprop-1-yl) piperidine dihydrochloride (12f)

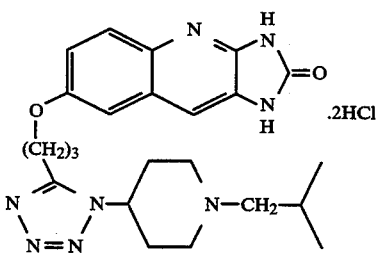

mp 258°–261° C.; IR (KBr, cm$^{-1}$) 3600–2300, 1730, 1622, 1368, 1232, 820; $^1$H NMR (300 MHz, DMSO-d$_6$) δ 1.00, (6H, d, J=6.6 Hz), 2.10 (1H, m), 2.28 (2H, m), 2.66 (2H, m), 2.90 (2H, t, J=6.0 Hz), 3.12 (2H, m), 3.60 (2H, m), 4.18 (2H, t, J=5.9 Hz), 4.87 (1H, m), 7.18 (1H, dd, J=9.1 and 2.7 Hz), 7.41 (1H, d, J=2.7 HZ), 7.64 (1H, s), 7.78 (1H, d, J=9.1 Hz), 10.56 (1H, brd, s), 11.31 (1H, s); −C NMR (75 MHz, DMSO-d$_6$) δ 21.04, 22.58, 25.11, 27.80, 30.05, 52.77, 53.57, 64.98, 68.33, 109.28, 112.53, 120.24, 127.30, 127.95, 128.23, 137.44, 146, 47, 156.26, 156.57, 156.79; MS m/e 451 (MH+).

Anal. calcd. for C$_{23}$H$_{30}$N$_8$O$_2$.2HCl.0.34 H$_2$O: C, 52.16; H, 6.22; N, 21.16. Found: C, 52.17; H, 6.10; N, 20.96.

EXAMPLE 11

[5-[3 -f 2, 3-Dihydro-2-oxo-1H-imidazo[4,5-b]quinolin-7-yloxy)propyl]-1H-tetrazol-1-yl]-1-(2-phenylethyl) piperidine dihydrochloride (12g)

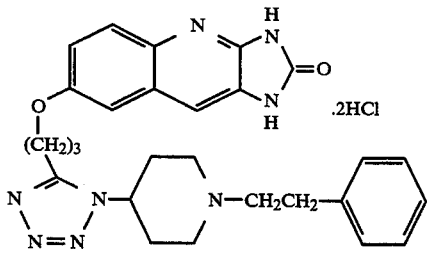

mp 238°–241° C.; IR (KBr, cm$^{-1}$) 3600–2300, 1720, 1622, 1242, 1154, 824, 752, 702; $^1$NMR (300 MHz, DMSO-d$_6$) δ 2.21, (4H, m), 2.45 (2H, m), 3.08 (6H, m), 3.22 (2H, m), 3.65 (2H, m), 4.12 (2H, t, J=5.7 Hz), 4.81 (1H, m), 7.09 (1H, dd, J=9.1 and 2.7 Hz), 7.25 (6H m), 7.50 (1H, s), 7.65 (1H, d, J=9.1 Hz); $^{13}$C NMR (75 MHz, DMSO-d$_6$) δ 19.37, 26.11, 28.76, 29.45, 50.47, 51.79, 56.51, 66.61, 107.39, 109.88, 118.16, 125.29, 126.44, 126.87, 127.74, 128.75, 128.84, 137.15, 137.48, 145.30, 154.63, 154.67, 155.36; MS m/e 499 (MH+).

Anal. calcd. for C$_{27}$H$_{30}$N$_8$O$_2$.2HCl.0.5H$_2$O: C, 55.86; H, 5.73; N, 19.30. Found: C, 55.86; H, 5.70; N, 18.84.

EXAMPLE 12

1-Cyclopentylmethyl-4-[5-[3-(2,3-dihydro-2-oxo-1H-imidazo[4,5-b]quinolin-7-yloxy)propyl]-1H-tetrazol-1-yl]piperidine dihydrochloride (12h)

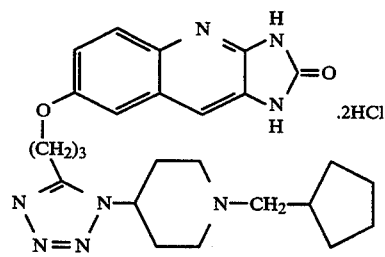

mp 237°–240° C.; IR (KBr, cm$^{-1}$) 2600–2400, 1734, 1622, 1238, 1154, 822; $^1$NMR (300 MHz, DMSO-d$_6$) δ 1.27, (2H, m), 1.55 (4H, m), 1.86 (2H, m), 2.17 (2H, m), 2.27 (4H, m), 2.61 (2H, m), 3.03 (2H, t, J=5.7 Hz), 3.15, (3H, m), 3.60 (2H, m), 4.17 (2H, t, J=5.8 Hz), 4.84 (1H, m), 6.3 (1H, brd s), 7.17 (1H, dd, J=9.1 and 2.7 Hz), 7.38 (1H, d, J=2.7 Hz), 7.60 (1H, s), 7.74 (1H, d, J=9.1 Hz), 10.69 (1H, brd s), 11.19 (1H, s), 11.5 (1H, brd s); $^{13}$C NMR (75 MHz, DMSO-d$_6$) δ 21.02, 26.35, 27.80, 30.20, 32.80, 36.22, 52.46, 53.50, 62.65, 68.26, 109.18, 112.02, 120.02, 127.13, 128.03, 128.84, 138.32, 146.73, 156.25, 156.44, 156.91; MS m/e 477 (MH+).

Anal. calcd. for C$_{25}$H$_{32}$N$_8$O$_2$.2HCl.0.9H$_2$O: C, 53.05; H, 6.38; N, 19.80. Found: 53.06; H, 6.04; N, 20.16.

---

126.39, 127.25, 136.78, 145.11, 154.61, 154.78, 155.28; MS m/e 491 (MH+).

Anal. calcd. for C$_{26}$H$_{34}$N$_8$O$_2$.2HCl: C, 55.42; H, 6.44; N, 19.88. Found: C, 55.00; H, 6.95; N, 19.41.

EXAMPLE 13

1-Cycloheptylmethyl-4-[5-[3-(2,3-dihydro-2-oxo-1H-imidazo[4,5-b]quinolin-7-yl-oxy)propyl]-1H-tetrazol-1-yl]piperidine dihydrochloride (12i)

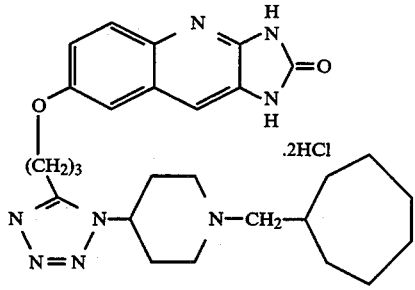

mp 224°–228° C.; IR (KBr, cm$^{-1}$) 3600–2400, 1722, 1622, 1450, 1240, 1154, 824; $^1$H NMR (300 MHz, DMSO-d$_6$) δ 1.24, (2H, m), 1.45 (4H, m), 1.58 (4H, m), 1.81 (2H, m), 1.97 (1H, m), 2.16 (2H, m), 2.28 (2H, m), 2.61 (2H, m), 2.90 (2H, t, J=5.9 Hz), 3.07 (2H, m), 3.16 (2H, m), 3.59 (2H, m), 4.17 (2H, t, J=5.8 Hz), 4.83 (1H, m), 5.2 (1H, brd s), 7.15 (1H, dd, J=9.1 and 2.7 Hz), 7.36 (1H, d, J=2.7 Hz), 7.56 (1H, s), 7.72 (1H, d, J=9.1 Hz), 10.28 (1H, brd s), 11.13 (1H, s), 11.54 (1H, brd s); $^{13}$C NMR (75 MHz, DMSO-d$_6$) δ 21.04, 27.00, 27.82, 29.53, 30.09, 33.66, 35.40, 52.83, 53.55, 64.25, 68.24, 109.11, 111.65, 119.86, 127.01, 128.10, 129.28, 138.97, 146.92, 156.27, 156.35, 157.00; MS m/e 505 (MH$^+$).

Anal. calcd. for C$_{27}$H$_{36}$N$_8$O$_2$.2HCl: C, 56.15; H, 6.63; N, 19.40. Found: C, 56.17; H, 6.78; N, 19.75.

EXAMPLE 14

[5-[3-(2,3-Dihydro-2-oxo-1H-imidazo[4,5-b]quinolin-7-yloxy)propyl]-1H-tetrazol-1-yl]-1-(2-propylpent-1-yl) piperidine dihydrochloride (12j)

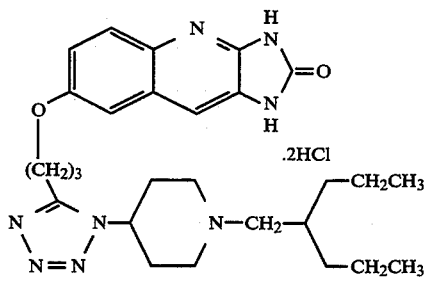

mp 189°–192° C.; IR (KBr, cm$^{-1}$) 3600–2400, 1720, 1624, 1364, 1242, 824; $^1$NMR (300 MHz, DMSO-d$_6$) δ 0.87, (6H, t, J=6.4 Hz), 1.30 (8H, m), 1.83 (1H, m), 2.17 (2H, m), 2.27 (2H, m), 2.62 (2H, In), 2.93 (2H, t, J=7.4 Hz), 3.14 (4H, m), 3.60 (2H, m), 4.16 (2H, t, J=5.7 Hz), 4.36 (2H, brd s), 4.82 (1H, m), 7.14 (1H, dd, J=9.1 and 2.7 Hz), 7.35 (1H, d, J=2.7 Hz), 7.55 (1H, s), 7.70 (1H, d, J=9.1 Hz), 10.37 (1H, brd s), 11.11 (1H, s); $^{13}$C NMR (75 MHz, DMSO-d$_6$) δ 15.84, 20.30, 21.05, 27.80, 30.09, 33.74, 35.09, 52.83, 53.58, 62.19, 68.24, 109.04, 111.56, 119.82, 126.96, 128.10, 129.38, 139.13, 146.96, 156.26, 156.32, 157.02; MS m/e (MH$^+$).

Anal. calcd. for C$_{27}$H$_{38}$N$_8$O$_2$.2HCl.0.36H2O: C, 55.34; H, 7.00; N, 19.12. Found: C, 55.32; H, 6.96; N, 19.46.

EXAMPLE 15

[5-[3-(2,3-Dihydro-2-oxo-1H-imidazo[4,5-b]quinolin-7-yloxy)propyl]-1H-tetrazol-1-yl]-1-[(terahydro-2H-pyran-2-yl)methyl]piperidine dihydrochloride (12k)

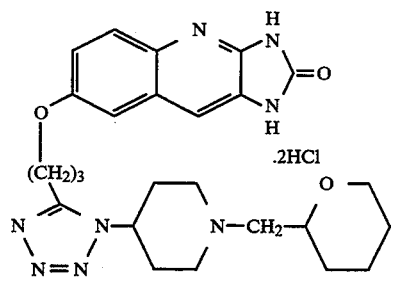

mp 245°–248° C.; IR (KBr, cm$^{-1}$) 3600–2300, 1722, 1624, 1224, 1156, 824; $^1$H NMR (300 MHz, DMSO-d$_6$) δ 1.18, (1H, m), 1.46 (2H, m), 1.53 (1H, m), 1.79 (1H, m), 2.17 (2H, m), 2.27 (2H, m), 2.49 (2H, m), 3.04 (4H, m), 3.14 (2H, t, J=7.1 Hz), 3.40 (2H, m), 3.60 (2H, m), 3.86 (2H, m), 4.15 (2H, t, J=5.7 Hz), 4.82 (1H, m), 4.99 (1H, brd s), 7.13 (1H, dd, J=9.1 and 2.7 Hz), 7.35 (1H, d, J=2.7 Hz), 7.56 (1H, s), 7.71 (1H, d, J=9.1 Hz), 10.73 (1H, brd s), 11.14 (1H, s), 11.54 (1H, brd s); $^{13}$C NMR (75 MHz, DMSO-d$_6$) δ 19.35, 22.42, 25.10, 26.13, 28.62, 28.85, 50.99, 51.69, 59.98, 66.58, 67.25, 71.65, 107.44, 110.02, 118.23, 125.36, 126.43, 127.60, 137.28, 145.26, 154.62, 154.70, 155.34; MS m/e 493 (MH$^+$).

Anal. calcd. for C$_{25}$H$_{32}$N$_8$O$_3$.2HCl: C, 53.10; H, 6.06; N, 19.81. Found: C, 52.63; H, 6.04; N, 19.56.

EXAMPLE 16

Ethyl 4-[5-[3-(2,3-dihydro-2-oxo-1H-imidazo[4,5-b]quinolin-7-yloxy)butyl]-1H-tetrazol-1-yl]-1-piperidine carboxylate (10b)

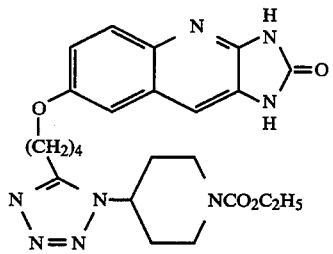

mp 233°–236° C.; IR (KBr, cm$^{-1}$) 3600–2600, 1738, 1720, 1684, 1622, 1440, 1236, 812; $^1$NMR (300 MHz, DMBO-d$_6$) δ 1.14, (3H, t, J=7.1 Hz), 1,82 (6H, m), 1.94 (2H, m), 2.97 (4H, m), 4.03 (6H, m), 4.65 (1H, m), 7.09 (1H, dd, J=9.1 and 2.7 Hz), 7.28 (1H, d, J=2.7 Hz), 7.45 (1H, s), 7.62 (1H, d, J=9.1 Hz), 10.91 (1H, s), 11.31 (1H, s); $^{13}$C NMR (75 MHz, DMSO-d$_6$) δ 14.59, 21.90, 23.25, 28.08, 31.48, 42.26, 53.93, 60.92, 67.17, 107.94, 109.42, 118.01, 125.10, 126.51, 128.14, 138.11, 145.41, 154.47, 154.60, 154.78, 155.44; MS m/e 481 (MH$^+$).

Anal. calcd. for C$_{23}$H$_{28}$N$_8$O$_4$.0.43H$_2$O: C, 56.57; H, 5.96; N, 22.94.

Found: C, 56.56; H, 5.75; N, 22.86

EXAMPLE 17

[5-[3-(2,3-Dihydro-2-oxo-1H-imidazo[4,5-b]quinolin-7-yloxy)butyl]-1H-tetrazol-1-yl]piperidine dihydrochloride (13a)

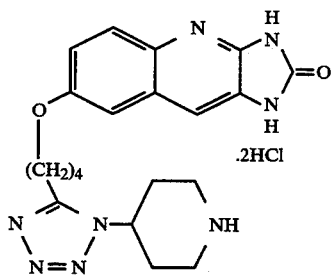

mp 315°–318° C.; IR (KBr, cm$^{-1}$) 3600–2200, 1756, 1684, 1234, 842; $^1$H NMR (300 MHz, DMSO-d$_6$) δ 1.90, (4H, m), 2.19 (2H, In), 2.30 (2H, m), 3.03 (2H, t, J=6.9 Hz), 3.11 (2H, m), 3.40 (2H, m), 4.12 (2H, t, J=5.6 Hz), 4.92 (1H, m), 7.22 (1H, dd, J=9.1 and 2.7 Hz), 7.44 (1H, d, J=2.7 Hz), 7.68 (1H, s), 7.80 (1H, d, J=9.1 Hz), 9.36 (1H, brd s), 9.58 (1H, brd s), 11.38 (1H, s); $^{13}$C NMR (75 MHz, DMSO-d$_6$) δ 23.67, 24.91, 29.76, 30.02, 43.67, 53.24, 69.03, 109.45, 113.00, 120.50, 127.42, 127.59, 127.89, 136.52, 146.17, 156.39, 156.68, 156.92; MS m/e 409 (MH+).

Anal-calcd. for C$_{20}$H$_{24}$N$_8$O$_2$.2HCl.0.31H$_2$O: C, 49.23; H, 5.51; N, 23.01. Found: C, 49.33; H, 5.35; N, 22.84.

EXAMPLE 18

[5-[3-(2,3-Dihydro-2-oxo-1H-imidazo[4,5-b]quinolin-7-yloxy)butyl]-1H-tetrazol-1-yl]-1-(phenylmethyl)piperidine dihydrochloride (13b)

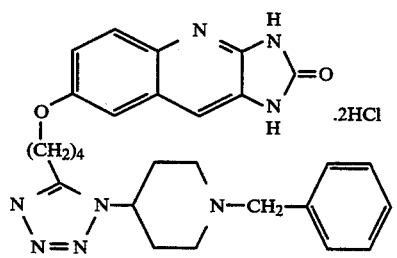

mp 203°–207° C.; IR (KBr, cm$^{-1}$) 3600–2400, 1744, 1624, 1240, 832, 750, 700; $^1$H NMR (300 MHz, DMSO-d$_6$) δ 1.88 (4H, m), 2.20 (2H, m), 2.54 (2H, m), 3.01 (2H, t, J=6.7 Hz), 3.11 (2H, m), 3.49 (2H, m), 4.11 (2H, t, J=5.4 Hz), 4.32 (2H, m), 4.81 (1H, m), 7.20 (1H, dd, J=9.1 and 2.7 Hz), 7.42 (1H, d, J=2.7 Hz), 7.46 (3H, m), 7.65 (3H, m), 7.78 (1H, d, J=9.1 Hz), ~8.2 (2H, brd s), 11.33 (1H, s), 11.65 (1H, brd s); $^{13}$C NMR (75 MHz, DMSO-d$_6$) δ 23.64, 24.87, 29.76, 30.19, 51.45, 53.44, 60.28, 68.98, 109.34, 112.64, 120.35, 127.31, 127.95, 128.03, 130.48, 131.14, 131.24, 133.43, 137.14, 146.35, 156.47, 156.78, 156.82; MS m/e 499

Anal. calcd. for C$_{27}$H$_{30}$N$_8$O$_2$.2HCl.1.05 H$_2$O: C, 54.93; H, 5.82; N, 18.98. Found: C, 54.93; H, 5.74; N, 18.87.

EXAMPLE 19

[5-[3-(2,3-Dihydro-2-oxo-1H-imidazo[4,5b]quinolin-7-yloxy)butyl]-1H-tetrazol-1-yl]-1-[(4-fluorophenyl)methyl)piperidine dihydrochloride (13c)

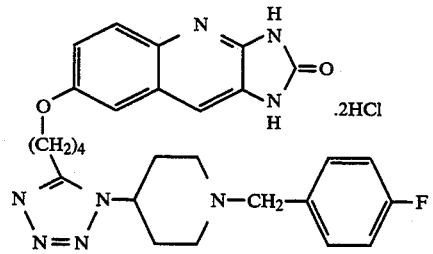

mp 229°–232° C.; IR (KBr, cm$^{-1}$) 3600–2300, 1746, 1640, 1234, 832; $^1$NMR (300 MHz, DMSO-d$_6$) δ 1.88 (4H, m), 2.20 (2H, m), 2.57 (2H, m), 3.01 (2H, t, J=6.9 Hz), 3.10 (2H, m), 3.49 (2H, m), 4.11 (2H, t, J=5.5 Hz), 4.33 (2H, m), 4.81 (1H, m), 7.20 (1H, dd, J=9.1 and 2.7 Hz), 7.31 (2H, t, J=8.8 Hz), 7.43 (1H, d, J=2.7 Hz), 7.67 (1H, s), 7.73 (2H, dd, J=8.6 and 5.6 Hz), 7.79 (1H, d, J=9.1 Hz), 8.85 (2H, brd s), 11.37 (1H, s), 11.71 (1H, brd s); $^{13}$C NMR (75 MHz, DMSO-d$_6$) δ 23.65, 24.85, 29.76, 30.18, 51.31, 53.42, 59.28, 68.99, 109.38, 112.84, 117.22, 117.51, 120.43, 127.38, 127.45, 127.77, 127.92, 135.76, 135.87, 146.24, 156.46, 156.72, 156.87; MS m/e 517 (MH+).

Anal. calcd. for C$_{27}$H$_{29}$FN$_8$O$_2$.2HCl.1.27H$_2$O: C, 52.95; H, 5.52; N, 18.29. Found: C, 52.96; H, 5.31; N, 18.22.

EXAMPLE 20

1-Cyclohexylmethyl-4-[5-[3-(2,3-dihydro-2-oxo-1H-imidazo[4,5-b]quinolin-7-yloxy)butyl]-1H-tetrazol-1-yl]piperidine dihydrochloride (13d)

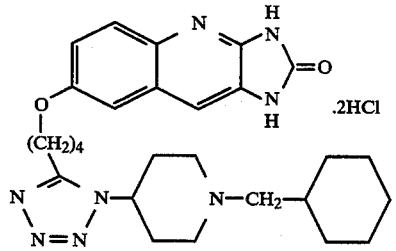

mp 253°–256° C.; IR (KBr, cm$^{-1}$) 3600–2400, 1744, 1640, 1624, 1238, 830; $^1$NMR (300 MHz, DMSO-d$_6$) δ 0.96, (2H, m), 1.20 (3H, m), 1.66 (3H, m), 1–83 (3H, m), 1.91 (4H, m), 2.18 (2H, m), 2.59 (2H, m), 2.88 (2H, m), 3.04 (2H, t, J=6.7 Hz), 3.12 (2H, m), 3.62 (2H, m), 4.13 (2H, m), 4.82 (1H, m), 5.33 (2H, very brd s), 7.18 (1H, dd, J=9.1 and 2.7 Hz), 7.39 (1H, d, J=2.7 Hz), 7.57 (1H, s), 7.72 (1H, d, J=9.1 Hz), 10.28 (1H, brd s), 11.13 (1H, s); $^{13}$C NMR (75 MHz, DMSO-d$_6$) δ 23.67, 24.88, 26.73, 27.19, 29.79, 30.16, 32.40, 33.95, 52.88, 53.46, 63.80, 68.92, 109.19, 111.72, 119.97, 127.01, 128.11, 129.13, 138.74, 146.82, 146.48, 156.61 156.98; MS m/e 505 (MH+).

Anal. calcd. for C$_{27}$H$_{36}$N$_8$O$_2$.2HCl.1.05H$_2$O: C, 54.37; H, 6.77; N 18.78. Found: C, 54.38; H, 6.61; N, 18.71.

EXAMPLE 21

[5-[3-(2,3-Dihydro-2-oxo-1H-imidazo[4,5-b]quinolin-7-yloxy)butyl]-1H-tetrazol-1-yl]-1-(2-ethybut-1-yl) piperidine dihyudrochloride (13e)

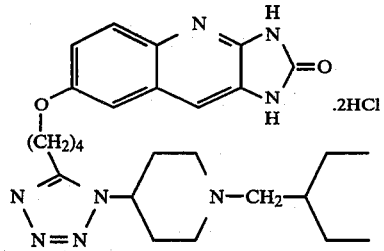

mp 239°–242° C.; IR (KBr, cm$^{-1}$) 3600–2400, 1746, 1640, 1624, 1358, 1238, 832; $^1$H (300 MHz, DMSO-d$_6$) δ 0.85, (6H, t, J=7.3 Hz), 1.41 (4H, m), 1.75 (1H, m), 1.91 (4H, m), 2.18 (2H, m), 2.66 (2H, m), 2.92 (2H, t, J=5.6 Hz), 3.05 (2H, t, J=6.8 Hz), 3.16 (2H, m), 3.63 (2H, m), 4.13 (2H, m), 4.84 (1H, m), 7.21 (1H, dd, J=9.1 and 2.7 Hz), 7.44 (1H, d, J=2.7 Hz), 7.65 (1H, s), 7.78 (1H, d, J=9.1 Hz), 10.58 (1H, brd s), 11.32 (1H, s); $^{13}$C NMR (75 MHz, DMSO-d$_6$) δ 11.83, 23.71, 24.89, 24.96, 29.78, 30.09, 36.58, 52.85, 53.61, 61.49, 68.98, 109.36, 112.56, 120.32, 127.30, 127.97, 128.12, 137.29, 146.39, 156.46, 156.78; MS m/e 493 (MH+).

Anal. calcd. for C$_{26}$H$_{36}$N$_8$O$_2$.2HCl.0.84H$_2$O: C, 53.78; H, 6.88; N, 19.29. Found: C, 53.78; H, 6.73; N, 19.02.

EXAMPLE 22

EXAMPLE 22

[5-[3-(2,3-Dihydro-2-oxo-1H-imidazo[4,5-b]quinolin-7-yloxy)butyl]-1H-tetrazol-1-yl]-1-(2-methylprop-1-yl) piperidine dihydrochloride (13f)

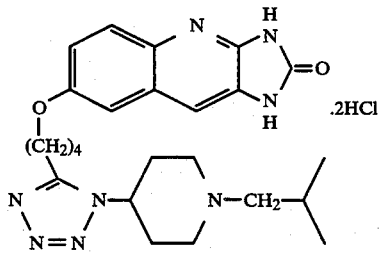

mp 225°–228° C.; IR (KBr, cm$^{-1}$) 3600–2300, 1744, 1642, 1624, 1360, 1240, 830; $^1$NMR (300 MHz, DMSO-d$_6$) δ 1.00, (6H, d, J=6.6 Hz), 1.91 (4H, m), 2.09 (1H, m), 2.18 (2H, m), 2.63 (2H, m), 2.89 (2H, t, J=6.2 Hz), 3.05 (2H, m), 3.11 (2H, m), 3.62 (2H, m), 4.13 (2H, m), 4.84 (1H, m), 5.56 (2H, brd s), 7.19 (1H, dd, J=9.1 and 2.7 Hz), 7.41 (1H, d, J=2.7 Hz), 7.60 (1H, s), 7.74 (1H, d, J-9.1 Hz), 10.36 (1H, brd, s), 11.19 (1H, s); $^{13}$C NMR (75 MHz, DMSO-d$_6$) δ 22.50, 23.68, 24.88, 25.10, 29.79, 30.09, 52.83, 53.50, 64.98, 68.94, 109.26, 112.02, 120.09, 127.11, 128.06, 128.77, 146.67, 156.48, 156.69, 156.91; MS m/e 465 (MH+).

Anal. calcd. for C$_{24}$H$_{32}$N$_8$O$_2$2.2HCl.1.35H$_2$O: C, 51.31; H, 6.58; N, 19.94. Found: C, 51.31; H, 6.33; N, 19.77.

What is claimed:
1. A compound of the formula

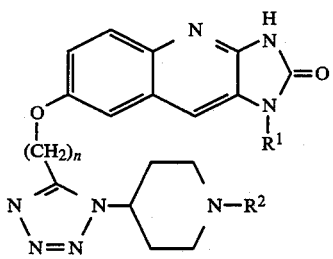

wherein
R$^1$ is H, or C$_1$–C$_4$ lower alkyl;
R$^2$ is H, or (CH$_2$)$_m$R$^3$;
R$^3$ is tetrahydro-2H-pyranyl, C$_1$–C$_8$ alkyl, C$_4$–C$_8$ cycloalkyl, or substituted or unsubstituted phenyl, wherein the substituents are halogen, alkoxy, or trifluoromethyl;
m is an integer of 1–3; and
n is an integer of 1–5;
or pharmaceutically acceptable salt thereof.

2. The intermediate compound which is ethyl 4-[5-[3-(2,3-dihydro-2-oxo-1H-imidazo[4,5-b]quinolin-7-yloxy)propyl]-1H-tetrazol-1-yl]-1-piperidinecarboxylate.

3. The compound of claim 1 which is [5-[3-(2,3-dihydro-2-oxo-1H-imidazo[4,5-b]quinolin-7-yloxy)propyl]-1H-tetrazol-1-yl]piperidine or pharmaceutically acceptable salt thereof.

4. The compound of claim 1 which is [5-[3-(2,3-dihydro-2-oxo-1H-imidazo[4,5-b]quinolin-7-yloxy) propyl]-1H-tetrazol-1-yl]-1-(phenylmethyl)piperidine or pharmaceutically acceptable salt thereof.

5. The compound of claim 1 which is [5-[3-(2,3-dihydro-2-oxo-1H-imidazo[4,5-b]quinolin-7-yloxy) propyl]-1H-tetrazol-1-yl]-1-[(4-fluorophenyl)methyl]piperidine or pharmaceutically acceptable salt thereof.

6. The compound of claim 1 which is (cyclohexylmethyl)-4-[5-[3-(2,3-dihydro-2-oxo-1H-imidazo[4,5-b]quinolin-7-yloxy)propyl]-1H-tetrazol-1yl]piperidine or pharmaceutically acceptable salt thereof.

7. The compound of claim 1 which is [5-[3-(2,3-dihydro-2-oxo-1H-imidazo[4,5-b]quinolin-7-yloxy) propyl]-1H-tetrazol-1-yl]-1-(2-ethylbut-1-yl) piperidine or pharmaceutically acceptable salt thereof.

8. The compound of claim 1 which is [5-[3-(2,3-dihydro-2-oxo-1H-imidazo[4,5-b]quinolin-7-yloxy) propyl]-1H-tetrazol-1-yl]-1-(2-methylprop-1-yl) piperidine or pharmaceutically acceptable salt thereof.

9. The compound of claim 1 which is [5-[3-(2,3-dihydro-2-oxo-1H-imidazo[4,5-b]quinolin-7-yloxy) propyl]-1H-tetrazol-1-yl]-1-(2-phenylethyl) piperidine or pharmaceutically acceptable salt thereof.

10. The compound of claim 1 which is 1-cyclopentylmethyl-4-[5-[3-(2,3-dihydro-2-oxo-1H-imidazo[4,5-b]quinolin-7-yloxy)propyl]-1H-tetrazol-1-yl]piperidine or pharmaceutically acceptable salt thereof.

11. The compound of claim 1 which is 1-cycloheptylmethyl-4-[5-[3-(2,3-dihydro-2-oxo-1H-imidazo[4,5-b]quinolin-7-yl-oxy)propyl]-1H-tetrazol-1-yl]piperidine or pharmaceutically acceptable salt thereof.

12. The compound of claim 1 which is [5-[3-(2,3-dihydro-2-oxo-1H-imidazo[4,5-b]quinolin-7-yloxy) propyl]-1H-tetrazol-1-yl]-1-(2-propylpent-1-yl) piperidine or pharmaceutically acceptable salt thereof.

13. The compound of claim 1, which is [5-[3-(2,3-dihydro-2-oxo-1H-imidazo [4,5-b]quinoline-7-yloxy)-propyl[-1H-tetrazol-1-yl]-1[(tetrahydro-2H-pyran-2- yl)methyl] piperidine or pharmaceutically acceptable salt thereof.

14. The intermediate compound which is ethyl 4-[5-[3-(2,3-dihydro-2-oxo-1H-imidazo[4,5-b] quinolin-7-yloxy)butyl]-1H-tetrazol-1-yl]-1-piperidine carboxylate.

15. The compound of claim 1 which is [5-[3-(2,3-dihydro-2-oxo-1H-imidazo[4,5-]quinolin-7-yloxy) butyl]-1H-tetrazol-1-yl]piperidine or pharmaceutically acceptable salt thereof.

16. The compound of claim 1 which is [5-[3-(2,3-dihydro-2-oxo-1H-imidazo[4,5-b]quinolin-7-yloxy) butyl]-1H-tetrazol-1-yl]-1-(phenylmethyl) piperidine or pharmaceutically acceptable salt thereof.

17. The compound of claim 1, which is [5-[3-(2,3-dihydro-2-oxo-1H-imidazo [4,5-b] quinolin-7-yloxy)-butyl]-1H-tetrazole-1-yl]-1-[(4-fluorophenyl)methyl]-piperidine or pharmaceutically acceptable salt thereof.

18. The compound of claim 1 which is 1-cyclohexylmethyl-4-[5-[3-(2,3-dihydro-2-oxo-1H-imidazo[4,5-b]quinolin-7-yloxy)butyl]-1H-tetrazol-1yl]piperidine or pharmaceutically acceptable salt thereof.

19. The compound of claim 1 which is [5-[3-(2,3-dihydro-2-oxo-1H-imidazo[4,5-b]quinolin-7-yloxy) butyl]-1H-tetrazol-l-yl]-1-(2-ethylbutyl) piperidine or pharmaceutically acceptable salt thereof.

20. The compound of claim 1 which is [5-[3-(2,3-dihydro-2-oxo-1H-imidazo[4,5-b]quinolin-7-yloxy) butyl]-1H-tetrazol-l-yl]-1-(2-methylpropyl) piperidine or pharmaceutically acceptable salt thereof.

21. A method for inhibiting blood platelet aggregation in a mammal which comprises administering a therapeutically effective amount of a compound of claim 1 or a pharmaceutically acceptable salt thereof.

22. The pharmaceutical composition for inhibiting blood platelet aggregation comprising a, therapeutically effective amount of a compound of claim 1 of a pharmaceutically acceptable acid addition salt thereof and a pharmaceutical carrier.

* * * * *